United States Patent [19]

Kaartinen et al.

[11] Patent Number: 4,689,203
[45] Date of Patent: Aug. 25, 1987

[54] CENTRIFUGE

[75] Inventors: Niilo Kaartinen, Kuusisto; Teuvo Sorvari, Turku, both of Finland

[73] Assignee: Fluilogic Systems Oy, Finland

[21] Appl. No.: 690,766

[22] Filed: Jan. 11, 1985

[30] Foreign Application Priority Data

Jan. 11, 1984 [FI] Finland .................................. 840087

[51] Int. Cl.⁴ .......................... G01N 9/30; G01N 1/18; G01N 21/07
[52] U.S. Cl. ..................................... 422/72; 422/101; 422/102; 436/45; 436/177; 356/426; 210/787
[58] Field of Search ................. 422/72, 101; 436/177, 436/45; 210/512.1, 512.3, 787; 356/426

[56] References Cited

U.S. PATENT DOCUMENTS

| | | | |
|---|---|---|---|
| 3,555,284 | 1/1971 | Anderson | 422/72 X |
| 3,681,029 | 8/1972 | Shapiro | 422/72 X |
| 3,825,175 | 7/1974 | Sartory | 233/2 |
| 3,890,101 | 6/1975 | Tiffany et al. | 422/72 X |
| 4,356,958 | 11/1982 | Kolobow et al. | 422/101 |
| 4,390,351 | 6/1983 | Matsui et al. | 210/512.1 |

FOREIGN PATENT DOCUMENTS

| | | |
|---|---|---|
| 42310 | 7/1970 | Finland . |
| 1405694 | 9/1975 | United Kingdom . |
| 1511819 | 5/1978 | United Kingdom . |
| 2025797 | 1/1980 | United Kingdom . |
| 2063719 | 6/1981 | United Kingdom . |
| 2064381 | 6/1981 | United Kingdom . |

*Primary Examiner*—Michael S. Marcus
*Assistant Examiner*—Lynn Kummert
*Attorney, Agent, or Firm*—Pahl, Lorusso & Loud

[57] ABSTRACT

The invention concerns a centrifuge intended for use in mainpulating liquid batches on an analytical scale. The centrifuge consists of a body (2) rotatable about its axis (1) provided with input and output conduits (8,9,11) and presenting the essential feature that therein are contained two parallel, circular arc-shaped volumes (3,4) located at different distances from the axis (1) of the body (2) constituting the center of curvature, and communicating with each other through a narrow gap (7) so that when the body is rotating, the heavier components of the liquid accumulate in the volume (4) further away from the axis, and the lighter components accumulate in the volume (3) closer to the axis, whereafter one of these two volumes can be emptied through a conduit (12), while the surface tension acting in the gap between the volumes keeps the liquid in the other volume in its place. The centrifuge of this invention is particularly appropriate for separating blood plasma from the red and white cells in the blood.

8 Claims, 5 Drawing Figures

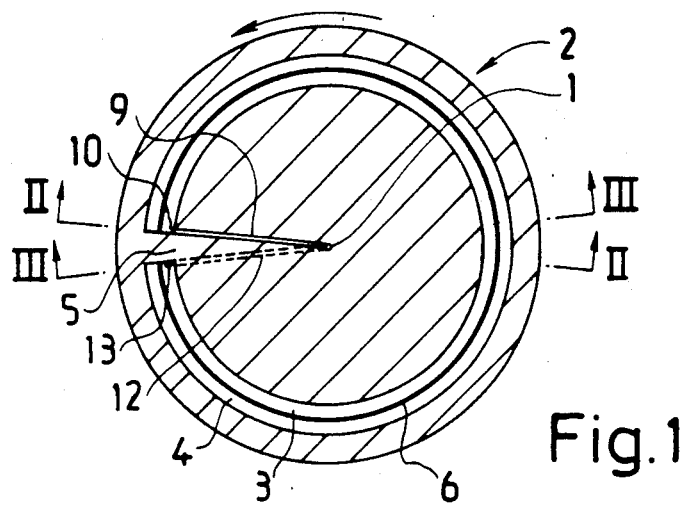
Fig.1
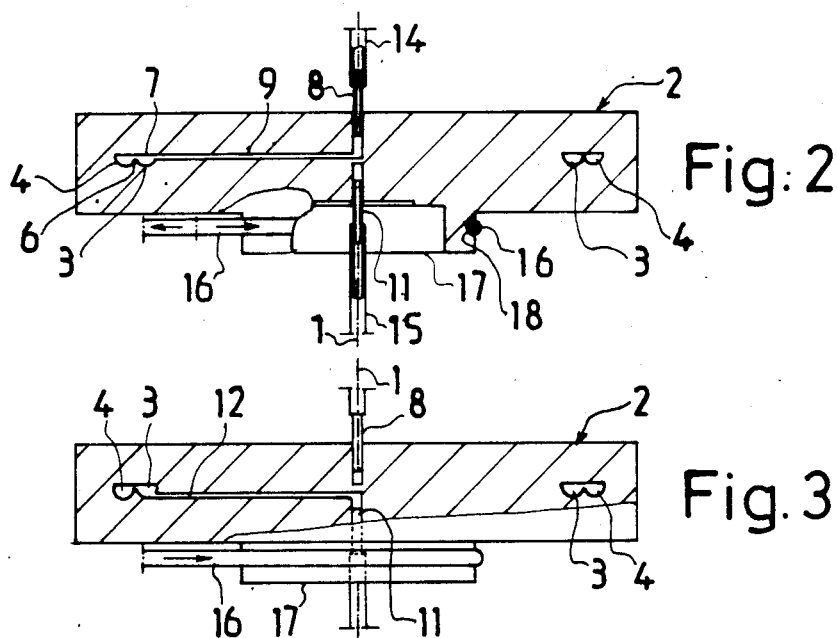
Fig.2
Fig.3
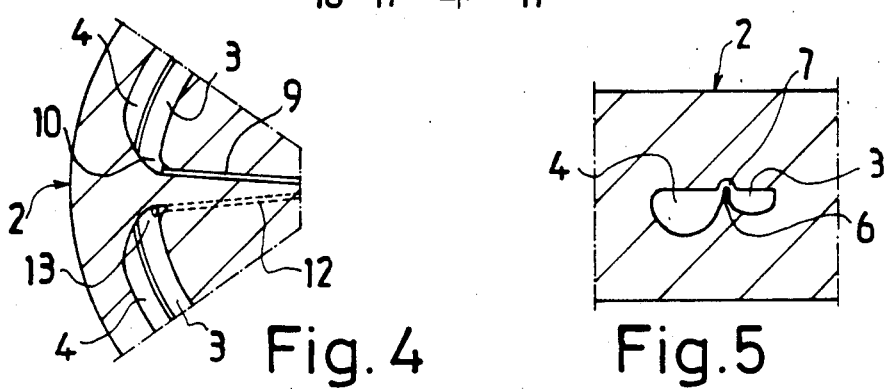
Fig.4
Fig.5

CENTRIFUGE

BACKGROUND OF THE INVENTION

The present invention concerns a centrifuge intended for manipulating liquids on an analytic scale, and consists of a body rotatable about its axis, this body comprising volumes in which separation of the liquid batch into components with different densities takes place, and conduits along which the liquid batch can be conducted into said volumes, so that the components of the liquid batch can be removed therefrom.

In manipulating small liquid batches on a laboratory scale, it is highly common practice to use centrifuges in which the liquid batch one wants to centrifuge is placed in a test tube. In such a case the placing of the liquid batch in the test tube and the removal of its components therefrom upon the conclusion of the centrifuging are mainly accomplished by manual labor. Also known in the art are centrifuging installations intended for manipulating larger liquid quantities in which the volume in which separation of the liquid into components takes place have been provided with conduits by which the liquid can be conducted into these spaces and its components can be removed therefrom upon the conclusion of the centrifuging. By using such apparatus, for instance, blood has been manipulated for separating the valuable blood plasma from the red and white cells.

Along with the advent of automatic analytic apparatus in clinical chemistry, the need has arisen to provide a centrifuge by which it would be possible to carry out the separation of small liquid batches into components, automatically by electronic control. The liquid batches to be manipulated would in the first place be blood samples, in which the plasma which constitutes the basis of the analyses must be separated from the red and white cells, which are irrelevant to the analysis. Therefore the centrifuge should comprise volumes in which the liquid, such as blood for instance, becomes divided into its components, an input conduit along which the liquid can be conducted into said volumes by electronic control, and a draining conduit by which the valuable component of the liquid, such as the blood plasma, is upon conclusion of the centrifuging under electronic control removable from the volumes, while at the same time the other components, such as the red and white cell masses, remains in its place.

The object of the present invention is to construct a centrifuge representing the analytic order of magnitude, i.e., one which is appropriate for manipulating liquid batches having a size between about 1 $\mu$l and 100 ml, by the aid of which the above-mentioned objective is achieved. It is characteristic of the invention that in the body constituting the centrifuge there are two parallel volumes shaped like a circular arc and located at different distances from the axis of the body constituting the center of curvature. The volumes communicate with each through a narrow gap so that as the body is rotating, heavier components of the liquid batch accumulate in the volume at a greater distance from the axis and the lighter components accumulate in the volume closer to the axis, whereafter one of these volumes can be emptied through a conduit, while at the same time the surface tension acting in the gap between the volumes keeps the liquid in the other volume in its place.

It is advantageous to construct the centrifuge of the invention so that it consists of a disk-like body in which the parallel volumes, in which separation of the liquid into its components takes place, have been formed to be concentric rings running around the body along its peripheral part and interrupted at one point, and in which input and output conduits for the liquid and for its components connect with the body on its cenytral axis, which constitutes the center of said rings, and run inside the body radially to the volumes in the peripheral part of the body.

When one component of the liquid is removed from the centrifuge after centrifuging, removal takes place from that volume of the centrifuge where the ends of the input and output conduits are located. When the centrifuge is intended to be used in manipulating blood samples, the ends of the conduits have to be located in the inner volume, that is the volume which lies closer to the axis of the body constituting the centrifuge, in which volume the plasma—being the ligher component of blood—accumulates in the course of centrifuging. Furthermore, in a centrifuge for blood samples, the volumetric proportion of the inner volume and the outer volume should be about 1:2, corresponding to the quantitative proportion of plasma and of red and white cells in blood.

An essential feature in view of the functioning of the centrifuge of the invention is the shaping of the parallel, circular arc-shaped volumes and of the gap therebetween so as to enable one volume to be emptied of the liquid present therein while the liquid in the other volume remains in its place. The shaping should, moreover, be such that the latter volume can also be caused to empty itself when the differential pressure between the input and output conduits associated with the volumes is sufficiently increased. In the case where the emerging liquid is waste, the emptying of said volume may be connected with the cleaning of the volumes, subsequent to centrifuging, with a suitable washing liquid and with compressed air.

It is advantageous to shape the parallel, circular arc-shaped volumes of the centrifuge so that they have a cross section resembling a cup and between them is left a similarly circular arc-shaped ridge over which there is a gap connecting the volumes substantially over their entire length. The height of the ridge is preferably such that the gap lies higher than the volumes, by which is avoided any remixing of the components upon conclusion of the centrifuging.

BRIEF DESCRIPTION OF THE DRAWINGS

The invention is described below in greater detail with the aid of examples, with reference made to the attached drawing, wherein:

FIG. 1 presents, viewed from above, a centrifuge according to the invention having parallel, substantially annular volumes in which separation of the liquid into its components takes place, FIG. 2 is the section II—II of FIG. 1, FIG. 3 is the section III—III of FIG. 1, FIG. 4 depicts, on a larger scale, the ends of the parallel volumes in the centrifuge and of the input and output conduits connecting therewith, according to another embodiment, and FIG. 5 presents on a larger scale a section of the parallel volumes belonging to the centrifuge, according to a third embodiment of the invention.

DETAILED DESCRIPTION OF THE PREFERRED EMBODIMENTS

In FIGS. 1-3 is depicted a centrifuge according to the invention, which is intended for manipulating liquid batches on an analytical scale. This centrifuge consists of a disk-like body 2 rotatable about its axis 1, the radius of which is on the order of 3.5 cm. The volumes 3,4 included in the body, in which the separation of the liquid batch into its components with different density takes place, consist of concentric rings, interrupted at one point 5, which run around the body in its peripheral part and of which the axis 1 constitutes the center. The volumes 3,4 have a cup-like cross section, and between the inner volume 3 and the outer volume 4 there is an annular ridge 6, over whichis left a gap 7 connecting the volumes over their entire length. Centrifuging is accomplished by rotating the body 2, whereby the component of the liquid with lower density accumulates in the inner volume 3 and the component with higher density accumulates in the outer volume 4.

For conducting the liquid batch to be manipulated into the volumes 3,4, and for removing its components from the volumes 3,4 after centrifuging, the body 2 has been provided with input and output conduits which are connected to the body axially on opposite sides thereof. The input conduit comprises a tubular part 8 integrally attached to the body 2 and parallelling the axis 1 of the body, and a part 9 in its continuation, which runs inside the body in the direction of the body's radius to the volumes 3,4. The end of the input conduit is located, as shown in FIG. 1, at one end 10 of the inner volume 3. Similarly, the output conduit comprises a tubular part 11 parallelling the axis 1 of the body and integrally connected with the body 2, and in its extension a part 12 running radially inside the body to the volumes 3,4. It is seen in FIG. 1 that the output conduit connects with the volumes 3,4 at the end 13 of the inner volume 3 which is opposite to the aforementioned end 10.

The tubular parts 8,11 belonging to the input and output conduits, which are integrally connected with the body 2 and therefore rotate along with it while centrifuging is going on, have been connected with stationary parts 14,15 on different sides of the body by disposing the parts one into the other at the juncture point, as shown in FIG. 2. The material of the parts 8,11, which are innermost at the junctures, is metal, and the material of the stationary parts 14,15, which are outermost at the junctures, is a fluoropolymer. The higher thermal expansion coefficient of the fluoropolymer causes the junctures to loosen through friction heat when the body 2 is being rotated. For this reason, the rotation of the body is in no way impeded by the junctures, and since the relative linear velocity between the metal and polymer surfaces owing to the small diameter (about 1 mm) of the pars will be low in spite of the high speeds of rotation of the body 2 (on the order of 100 r.p.s.), there also cannot occur any significant abrasion of the parts at the junctures. When the rotation of the body 2 is terminated, the junctures are automatically resealed as the parts cool, and it is therefore possible through them to carry out the required transfers of liquid batches and the cleaning of the concentric volumes 3 and 4.

Rotation of the body 2 has, in the centrifuge depicted here, been implemented using a belt drive. For the belt 16, a round projection 17 has been furnished on the body 2, having a groove 18 for the belt.

The centrifuge just described is operated by filling the volumes 3,4 in the body 2 with the liquid batch which one desires to centrifuge, this liquid batch being introduced through the input conduit 8,9. The body 2 is thereafter set in rotation, whereby the heavier component of the liquid under centrifugal force action accumulates in the outer volume 4, with the lighter component accumulating in the inner volume. After stopping the body 2, the lighter component is removed from the volume 3 into the output conduit 12,11 by the aid of a differential pressure arranged to act between the input and output conduits. This differential pressure is selected so that the heavier component in the outer volume 4 will during removal of the lihgter component remain in its place by effect of the surface tension acting in the gap 7 between the volumes. Removal of the component in the outer volume 4 is thereafter effected by increasing the differential pressure between the input and output conduits enough for the pressure to overcome the surface tension acting in the gap 7 and to push the liquid in the outer volume into the inner volume and further into the output conduit 12.

The concentric volumes 3,4 of the centrifuge of the invention have in FIGS. 1-3 been depicted with the simplest possible configuration. In FIGS. 4 and 5 there is shown a shaping of the ends of volumes 3,4 differing from FIGS. 1-3 and a cross-sectional shape of the volumes in which the endeavour has been to eliminate corners where the liquid might stagnate and impede the cleaning and drying of the volumes. Furthermore, it is essential in the shaping of the volumes 3,4 as in FIG. 5 that the crown of the ridge 6 between the volumes is on a level with the topmost parts of the volumes so that the gap 7 connecting the volumes, located on top of the ridge, lies at a higher elevation than the volumes. The volumetric proportion of the inner volume 3 and the outer volume 4 is here about 1:2, which corresponds to the quantitative proportion of blood plasma and red and white cells in the blood.

It is obvious to a person skilled in the art that different embodiments of the invention are not confined to the examples presented in the foregoing and that they may instead vary within the scope of the claims following below.

We claim:

1. A centrifuge for use in the treatment of batches of liquid on an analytical scale including a body rotatable about an axis, said body comprising two parallel concentric arc-shaped chambers such that the chambers form cöncentric rings interrupted at one point, wherein said chambers have ends facing towards each other but not connecting at said one point, each of said chambers extending for a length around said body, said chambers being located at different radial distances from the axis of the body wherein said axis is a center of curvature for said arc-shaped chambers, said chambers communicating with each other through a narrow gap of capillary dimensions substantially over their entire lengths and said chambers being shaped so as to enable a free separation of a batch of liquid which is filling the chambers into a heavier component accumulating in the chamber radially further away from the axis and into a lighter component accumulating in the chamber radially closer to the axis, and said body further comprising input and output conduits for filling the chambers with a batch of liquid and for separately removing the lighter and heavier components, respectively as obtained in the separation, the conduits being connected to the ends of only the innermost chamber so as to enable removal of the lighter component from that chamber while holding the heavier component in the outer chamber with the aid of the surface tension acting in the gap between the chambers, the removal of the heavier component being then effected with an added pressure overcoming the surface tension.

2. A centrifuge according to claim 1, wherein the inner chamber and the outer chamber have a volumetric proportion of about 1:2, respectively, in which case the centrifuge is particularly appropriate for separating the plasma in blood samples from the red and white cells.

3. A centrifuge according to claim 1 wherein said body is a disk-like body and said parallel, arc-shaped chambers are circular and are located in a peripheral portion of the disk-like body and in which the input and the output conduits are axially connected to the body and are further disposed inside the body extending radially outwardly to the chambers in the peripheral portion of the body.

4. A centrifuge according to claim 3, wherein the input conduit is axially connected to the body on one side thereof, and the output conduit is axially connected to the body on an opposite side thereof, wherein at least one of said conduits comprises a tubular part belonging to the body and rotating together therewith and having a stationary part extending therefrom axially outwardly from said body, said tubular and said stationary parts being disposed at the juncture point of the input and output conduits, wherein the tubular part is positioned within the stationary part and said stationary part is made of a material having a higher thermal expansion coefficient than the material of the tubular part.

5. A centrifuge according to claim 4, wherein the tubular part of said at least one of said conduits comprises metal and the stationary part comprises a fluoropolymer.

6. A centrifuge according to claim 1, wherein the parallel, arc-shaped chambers are circular and have a curved ridge disposed therebetween wherein a gap is present above said curved ridge connecting the chambers substantially over their entire lengths.

7. A centrifuge according to claim 6, wherein the chambers have a cup-like cross section.

8. A centrifuge according to claim 6, wherein said curved ridge is disposed such that the gap is located at a higher elevation than said chambers.

* * * * *